United States Patent [19]

Ben-Bassat et al.

[11] Patent Number: 5,114,849
[45] Date of Patent: May 19, 1992

[54] PROTECTANTS FOR MICROBIAL FERMENTATION

[75] Inventors: Arie Ben-Bassat, Walnut Creek; Kent D. Coddington, El Cerrito, both of Calif.; Donald C. Johnson, Auburn, Wash.

[73] Assignee: Weyerhaeuser Company, Wash.

[21] Appl. No.: 604,587

[22] Filed: Oct. 26, 1990

[51] Int. Cl.$^5$ ............................................. C12P 19/04
[52] U.S. Cl. ...................................... 435/101; 536/56; 536/124
[58] Field of Search .................. 435/101; 536/56, 124; 525/54.1, 54.21

[56] References Cited

U.S. PATENT DOCUMENTS 2,910,410 10/1959 Corman .
4,863,565 9/1989 Johnson et al. .
4,871,665 10/1989 Viehweg .
4,929,550 5/1990 Byrom .

FOREIGN PATENT DOCUMENTS 228779 2/1987 European Pat. Off. .
90-12098 10/1990 PCT Int'l Appl. .

OTHER PUBLICATIONS

Shinobu et al., Chemical Abstracts, vol. 73, Sep. 28, 1970, #7-37-85b.
Gashinskii et al., Chemical Abstracts, vol. 102, May 13, 1985, #163619x.
Gashinskii et al., Chemical Abstracts, vol. 109, Dec. 5, 1988, #208192r.
Harris, et al., (1973), *Ann. Rev. Microbiol* 27:27-50.
Mizrahi, A., (1984) *Develop biol. Standard* 55:93-102.
Goosens and Luner, (1976) *Tappi* 59:89-94.
Magnifloc ® 833A product specification report, (1987) American Cyanamid Company.
Magnifloc ® 985N product specification report, (1987) American Cyanamid Company.
Floxan ® EA-1340 Product Bulletin, (1985) Henkel Corporation.
Floxan ® SC-5062, Floxan ® SC-5067, Floxan ® SC-5080, Floxan ® SC-5082 Product Bulletin, Henkel Corporation.
Floxan ® EC-2000 Product Bulletin, Diamond Shamrock Chemicals Company.
Product Data sheet, Tecna Corporation.
Reten ® 420 Product Data sheet, (1989) Hercules, Incorporated.
Reten ® 421, 423 and 425 Product Data sheet, (1989) Hercules, Incorporated.
Cyanamer ® polyacrylamides, For the Processing Industries, (1982), American Cyanamid Company (pp. 1-24).

*Primary Examiner*—Ronald W. Griffin
*Assistant Examiner*—Pamela S. Webber
*Attorney, Agent, or Firm*—Albert P. Halluin; Elizabeth F. Murphy

[57] ABSTRACT

The present invention provides an improved process for the production of microbial cellulose where a cellulose-producing organism is grown under agitated conditions in the presence of a polyacrylamide-containing polymer.

18 Claims, 1 Drawing Sheet

PROTECTANTS FOR MICROBIAL FERMENTATION

FIELD OF THE INVENTION

The invention relates to microbial fermentation processes and, more particularly, to an improved process for the production of cellulose by microbial fermentation.

BACKGROUND OF THE INVENTION

Cellulose is produced by plants and by various microorganisms. Examples of cellulose producing prokaryotic organisms include Acetobacter, Rhizobium, Agrobacterium and Aztobacter. Harris et al., (1973) Ann Rev Microbiol 27:27-50. Acetobacter is one of the best characterized cellulose producing organisms.

Acetobacter is characteristically a Gram-negative, rod-shaped bacterium 0.6-0.8 um by 1.0-4 um. It is strictly aerobic, metabolism is respiratory, never fermentative. It is further distinguished by its ability to simultaneously produce multiple poly-$\beta$(1-4) glucan chains, which are chemically identical to cellulose. Multiple cellulose chains or microfibrils are synthesized at sites on the bacterial cell wall. These microfibrils are extruded by the bacterium into the culture medium.

The cellulose microfibrils produced by Acetobacter have cross-sectional dimensions of about 1.6 nm $\times$ 5.8 nm. In static or standing cultures, the microfibrils at the bacterial surface combine to form a fibril having cross-sectional dimensions of about 3.2 nm $\times$ 133 nm. This small cross-sectional width is the chief difference between cellulose produced by Acetobacter and cellulose found in wood pulp. The small cross-sectional size of these Acetobacter-produced fibrils, together with the concomitantly greater surface area than conventional wood-pulp cellulose and the inherent hydrophilicity of cellulose, leads to a cellulose product having unusually great capacity for absorbing aqueous solutions. This capacity for high absorbency has led to the development of several products from Acetobacter cellulose, such as wound dressings and paper products.

In 1947, Hestrin et al, (1947) Nature 159:64-65 found that in the presence of glucose and oxygen, non proliferating cells of Acetobacter synthesize cellulose. Since that time, Acetobacter has been cultured under a variety of conditions which support cellulose production. For example, when grown with reciprocal shaking at about 90-100 cycles per minute, cells have been incorporated into a large gel mass. When grown under conditions in which the culture medium is agitated with swirling motion for four hours, stellate gel bodies form which are comprised of cellulose and cells. When grown as standing cultures, a pellicle forms at the air/medium interface. The pellicle forms as a pad generally having the same surface shape and area as the liquid surface of the vessel containing the culture. Hestrin and Schramm, (1954) *Biochem J* 58:345-352.

In static cultures, production of cellulose by Acetobacter occurs at the air-liquid medium interface. Acetobacter is an obligate aerobe, therefore each bacterium continuously produces one fibril at the air-liquid interface. As new cellulose is formed at the surface, existing cellulose is forced downward into the growth medium. As a result, cellulose pellicles produced in static culture conditions consist of layers of cellulose fibers which support the growing Acetobacter cells at the air medium interface. Significantly, the volume of cellulose so produced is restricted by the interface between air and culture medium.

Acetobacter also produce cellulose when grown in agitated cultures. However, for several reasons, high cellulose productivity from agitated cultures has previously been difficult to attain. The tendency of known Acetobacter strains to become non-producers when cultured under agitated conditions at increased dissolved oxygen concentration has in the past severely limited the amount of cellulose that can be made economically. U.S. Pat. No. 4,863,565 discloses a number of strains of Acetobacter that are stable in long term cultures under both agitated and static conditions. That patent describes selected Acetobacter strains characterized by a sharply reduced ability to form gluconic and keto-gluconic acids when grown on a glucose containing medium. The strain used in the present invention, strain 1306-21, is one of the stable strains disclosed in that patent.

A second problem that has limited cellulose production in agitated cultures stems from the high agitation rates required to oxygenate the fermentation medium as the cellulose and cell concentrations of the culture increase. Oxygen demand of a culture increases as the cell density of the culture increases. Further, at high cellulose concentrations the fermentation broth becomes more viscous, thus the oxygen transfer rate from the air phase to the liquid phase decreases. Therefore, increasing agitation rates are required to sustain sufficient levels of dissolved oxygen in the culture to maintain cell growth and cellulose production. However, the increased agitation negatively affects the amount of cellulose produced due to a substantial decrease in cellulose yield and volumetric productivity.

Cellulose production by Acetobacter has been shown to decrease as the agitation rate of the culture is significantly increased (see, for example, the data provided in Example 1, infra). Increasing the agitation rate may adversely affect the cellulose to cell ratio and/or the cellulose yield of the culture. These effects may be attributable to increasing shear stress on the cells and cellulose as the agitation rate of the culture is increased. At high agitation rates, the quality of the cellulose produced is also affected. See, for example, U.S. Pat. No. 4,863,565 which discloses that in tests in a fermentor (14 liters) using an impeller to agitate the broth, it was found that the characteristics of the broth (viscosity) and the resulting cellulose (particle size and morphology, settling rate, hand sheet formation) were affected by high impeller speeds (above about 600 rpm in the runs carried out). These effects were more pronounced the longer the cultures were agitated at such speeds.

The present invention discloses the use of polyacrylamides and closely related anionic copolymers. The closely related anionic copolymers are formed from combined polymerization of acrylamide and acrylic acid (or its salts) or partial hydrolysis of amide functional groups of a polyacrylamide.

Polyacrylamides are used for many different purposes. They are commonly used as flocculating agents to clarify liquids. Some of the uses of polyacrylamides include sludge thickening, polymer recovery, crystal control, and use as aids in dewatering. The compounds can also be used as aids in vacuum filtration and centrifugation to increase production rate and cake solids capture.

SUMMARY OF THE INVENTION

The present invention describes an improved process for the production of microbial cellulose in agitated cultures. The effect of the improved process described herein is typified by the enhanced cellulose volumetric productivity and enhanced yield observed when the process is employed to grow agitated flask and fermentor cultures of cellulose producing microorganisms.

The present invention discloses a process for the aerobic production of microbial cellulose in an agitated culture of microbial cells capable of producing cellulose, grown in a suitable nutrient growth medium, wherein the process comprises the steps:

(a) culturing the microbial cells in the presence of an agent comprising a polyacrylamide containing polymer having a weight average molecular weight in the range of about $10^6$ to about $10^7$ daltons at a concentration effective to improve cellulose yield from an agitated culture; and (b) recovering the microbially produced cellulose.

Preferred polyacrylamide-containing polymers effective in stimulating the greatest increase in cellulose yield in the agitated cultures are high molecular weight polymers having a weight average molecular weight range of about $10^6$ to about $10^7$ daltons. Among these high molecular weight polyacrylamide-containing polymers which stimulated the greatest increase in cellulose product were nonionic or anionic polymers. Strongly cationic polymers were generally found to be toxic to cell growth.

MODES OF CARRYING OUT THE INVENTION

Cell growth and cellulose production in static and agitated cultures of cellulose producing microorganisms such as, for example, Acetobacter, can be limited due to insufficient supply of dissolved oxygen to the culture medium. However, while an increase in the agitation rate can result in enhanced cell growth, the increased agitation rate does not correspondingly increase cellulose production. In fact, as the agitation rate of cellulose producing microbial cultures is increased, the cellulose yield decreases. While not wishing to be bound by any particular theory, it is likely that the shear stress resulting from the higher agitation rates has an adverse effect on cellulose yield.

The present invention discloses suitable polyacrylamide containing polymers effective to protect the cellulose produced in agitated cultures of cellulose producing microorganisms from the reduction in cellulose yield and volumetric productivity that is associated with high agitation. As used herein, the term "polyacrylamide-containing polymer" refers to a polymer comprised of acrylamide monomers. "Polyacrylamide containing polymer" is not limited to polymers consisting solely of acrylamide monomers, but also includes, for example, co-polymers of acrylamide and sodium acrylate. The use of said polyacrylamide-containing polymer at concentrations in the range of about 0.1 g/L to about 5.0 g/L, more preferably about 0.4 g/L to about 3 g/L, has been found to enhance cellulose yield from agitated fermentation cultures.

Any microbial strain capable of producing cellulose may be used in the process of the invention. Suitable strains include strains belonging to the genus Acetobacter, for example, strains of the deposited species Acetobacter strain 1306-3 and derivatives thereof. As used herein, "Acetobacter" refers to a genus of microorganisms, and in particular to members of that genus which produce cellulose. Acetobacter strain 1306-21 was derived by mutagenizing strain 1306-3 and selecting an isolate which produced lower levels of gluconic acid. The preparation and identification of strain 1306-21 is described in U.S. Pat. No. 4,863,565. Strain 1306-21 was found to exhibit lower acid production and greater cellulose yield than the other isolates screened. Acetobacter strains 1306-3 and 1306-21 are on deposit at the American Type Culture Collection (ATCC), Rockville, Md., U.S.A. under the depository numbers ATCC 53264 and 53524, respectively. These strains were deposited under the terms of the Budapest Treaty on the International Recognition of the Deposit of Microorganisms for the Purposes of Patent Procedure and Regulations thereunder (Budapest Treaty).

Recombinant strains of cellulose producing organisms may also be used in the process of the invention. Suitable host cells containing all or parts of the cellulose synthase operon from *Acetobacter xylinum* are one embodiment of the invention. Strain 1306-3 pUC18-824 pABCD, a recombinant Acetobacter strain carrying genes A, B, C, and D of the cellulose synthase operon is described in U.S. patent application Ser. No. 496,236. The plasmid pABCD has been deposited at the American Type Culture Collection in an *E. coli* host (*E. coli* DG101 pUC18-824 pABCD) under the depository number ATCC 68264.

Various feed stocks may be used as the carbon source for growth of the cellulose producing microorganisms according to the process of the invention. Appropriate carbon sources include monosaccharides and mixtures thereof such as, for example, glucose and fructose, and disaccharides such as, for example, sucrose, in pure or partially purified form or as monosaccharide and disaccharide-containing stocks such as hydrolyzed corn starch, hydrolyzed wood and molasses. Casein hydrolysate, protein hydrolysate, yeast extract, malt extract, ammonium salts, corn steep liquor and other nitrogen rich substances can be used as a general source of amino acids, nitrogen, minerals and vitamins.

Bacterial cultures may be grown under agitated culture conditions by any means known to generate turbulence in the liquid culture medium. Such means are well known to those skilled in the fermentation arts. At small scale, generally less than 1 liter culture volume, liquid cultures may be agitated by reciprocal or shaking incubators, which impart a swirling motion to the medium.

Various reactor designs may be appropriate for the large scale production of the cellulose product according to the invention. See, e.g., Chapter 7 of Biochemical Engineering and Biotechnology Handbook, Atkinson and Mavitnua, eds., 1st Ed. The Nature Press N.Y., 1983. For large scale cellulose production, generally culture volumes exceeding 1 liter, the culture broth may be agitated by a number of means including various types of impellers, buoyant lift fermentors including air lift fermentors, pump driven recirculation of the fermentor broth or combinations thereof. Desirable characteristics for the fermentor impellers include high mass transfer rates, high circulation rates and low shear stress.

So long as the culture medium is agitated, various fermentation methods are appropriate for growing the cellulose producing microorganism at an average volumetric productivity for cellulose, which is within the scope of the invention, of at least 0.1 g/L/hr for sustained periods of time. Appropriate fermentation methods include batch fermentation, fed batch fermentations, repeated batch fermentation, and continuous fermentation, In batch fermentations the cellulose producing microorganism is inoculated into a fermentation vessel and the fermentation proceeds without further addition of culture media. At the end of the fermentation, the contents of the fermentation vessel are collected and the cellulose is removed. In fed batch fermentations, various nutrients, such as carbon source or nitrogen source are added to the medium during the fermentation run without removing the fermentation broth for processing until the end of the fermentation run. The nutrients may be added continuously, at predetermined intervals or when nutrient levels in the medium fall below desired values. In repeated batch fermentations, a volume of the culture broth is removed for processing, a volume of fresh medium is added to the culture broth remaining in the culture vessel, and the fermentation is resumed. In repeated batch fermentations, as in fed batch fermentations, the nutrients may be added continuously, at predetermined intervals or when nutrient levels in the medium fall below desired values. In continuous fermentations, the broth is removed from the fermentation vessel and replaced with fresh medium at a constant rate. In continuous fermentations, by adjusting the flow of medium into and culture broth out of the vessel the specific growth rate of the cellulose producing-microorganism can be maintained at an approximately constant rate.

Batch fermentations, fed batch fermentations, repeated batch fermentations, and continuous fermentations are all suitable for achieving an average volumetric productivity of at least 0.1 g/L/hr. so long as the inoculum of the culture medium is initially at least 1% (v/v). An inoculum in a range of 1-10% (v/v) of the culture medium is effective to obtain an average volumetric productivity of cellulose of 0.1 g/L/hr. An inoculum of about 5-10% (v/v) of the culture medium is preferred. In continuous cultures, as medium, cellulose producing cells and cellulose are removed, fresh medium will be added at a rate sufficient to maintain the volumetric productivity at an average of at least 0.1 g/L/hr.

In the present invention, protectants are defined as chemicals that enhance cellulose yield at high agitation growth conditions. These protectants may be identified in a three step process. An initial screen of potential protectants is performed in shake flasks. Each protectant is tested for its ability to enhance biomass production in a separate culture that is agitated at 375 rpm for 3 days. Biomass corresponds to the mass of cells and cellulose. Our studies have shown that cellulose production and yield are very sensitive to agitation while cell growth is significantly less sensitive. Therefore, changes in biomass concentration can be used as an indicator for shear stress damage and protection by a protectant.

The protectants are tested at concentrations ranging from 0.4 g/L-5 g/L. The biomass concentration of each test culture is compared to biomass concentrations of control cultures, which lack protectants and are agitated at either 125 or 375 rpm. The test cultures are screened to determine which protectants give the highest biomass concentrations, relative to the 375 rpm control culture. The biomass concentrations of the test cultures will not necessarily be higher than that of the 125 rpm control culture.

The most promising protectants, i.e., those that yield the highest biomass concentrations at high agitation rates in the initial screen, are then tested to determine their optimal concentrations. Each protectant is tested within a concentration range of 0.1-5 g/L. Generally, a protectant concentration of about 1 g/L most enhances biomass production.

Protectants which show promising results in the first two steps of the screen are then tested in a laboratory scale fermention, e.g., in a 14 liter Chemap fermentor. Protectants are generally first tested in the fermentors at 1 g/L. During the fermentor runs, samples are removed and cell concentration, cellulose concentration, yield, volumetric productivity and cellulose/cell ratios are determined.

The polyacrylamide-containing polymers having a ht average molecular weight in the range of about $10^6$ to about $10^7$ daltons are the most effective protectants and cells cultured in the presence of the high molecular weight polymers show the greatest increases in cellulose yield. Generally, the most effective polymers are nonionic or anionic. Strongly cationic polymers have generally been found to be toxic. Specific examples of polyacrylamide containing polymers which increase cellulose yield when added to agitated cultures include:

Magnifloc ® 833A is a high molecular weight anionic flocculant manufactured by American Cyanamid Company. Its typical properties include:

| Appearance | Off-white, granular powder |
| --- | --- |
| Degree of anionic charge | High |
| Bulk density | 50-56 lb/ft$^3$ |
| | (800-900 kg/m) |
| pH of 0.5% solution at 25° C. (77° F.) | 7.5-9.5 |

| Viscosity,* cps. | |
| --- | --- |
| % solution | 25° C. |
| 0.1 | 150 |
| 0.25 | 450 |
| 0.5 | 900 |

*Brookfield

Floxan ® EA-1340 is an anionic polyacrylamide oil-in-water emulsion manufactured by Henkel Corporation. Its composition and physical properties include:

| | Contents (% Wt/Wt) |
| --- | --- |
| Material | |
| Polyacrylamide solution | >75.5 |
| Kerosene | 24.0 |
| Acrylamide | <0.5 |
| Physical Data: | |
| Appearance | Opague off-white liquid |
| Odor | Hydrocarbon odor |
| Specific Gravity (Water = 1) | 1.00 |
| Solubility in Water, | Appreciable. Very viscous at |
| % by Weight | greater than 3% |

Polytec polyacrylamides, manufactured by Tecna Corporation, are high molecular weight polyacrylamides. Their typical properties include:

| Polytec Type | 31 | 36 |
| --- | --- | --- |
| Anionic Functionality | Nonionic | Med-High |
| Particle Size (mesh-mm) | 1.5 | 1.5 |
| Bulk Density (LB/CF) | 47 | 50 |
| Color | White to Off-White | |
| Moisture Content % | 11 | 11 |
| pH 5% Solution | 7.0 | 7.0 |
| Average Viscosity (cps) | | |
| 0.5% | 80 | 1500 |
| 0.25% | 30 | 600 |
| Max. Recommended Conc. % | 1.0 | 0.5 |
| Dissolution Time (min) | 90 | 60 |

The Reten® polyacrylamides, manufactured by Hercules, Incorporated, have the following properties:

| | Reten ® 420* | Reten ® 423* |
| --- | --- | --- |
| Anionic Functionality | None | Moderate |
| Bulk density, lbs/cu ft | 42 | 42 |
| Volatiles, % | 15 max | 15 max |
| Residual monomer, % | 0.2 max | 0.2 max |
| Screen analysis, % through U.S. 20 | 99 | 99 |
| Solution, 1% at 25° C. (77° F.) pH | 7-9 | 7.5-8.5 |
| Viscosity, Brookfield LVF, 60 rpm, cps | 300-500 | 3000-4000 |

*According to the manufacturer, these values should not be construed to be product specifications.

The experiments described herein disclose that culture medium stored with the polyacrylamide-containing polymer in it will deteriorate over time. The greatest increase in cellulose yield is observed when the protectant is added to the culture medium immediately prior to use. The experiments described herein also disclose that storage of the polyacrylamide containing polymer as an aqueous solution prior to addition to the culture medium does not appear to adversely affect the ability of the protectant to enhance cellulose yield.

Further experiments disclose that sterilization of the protectant in the presence of corn steep liquor (CSL) significantly reduces the ability of the protectant to enhance cellulose yield. Therefore, it is preferred to sterilize the desired protectant independently of the CSL and to store the protectant separately from the culture medium.

The effective pH range for culturing the cellulose producing microorganisms according to the invention is between 4 and 6, with a preferred range of 4.5 to 5.5, and most preferred pH 5.0. pH may be controlled by means of buffers such as citrate or 3,3 dimethylglutaric acid (DMG) added to the culture medium; or the addition of base or acid to the medium in an amount sufficient to maintain pH in the desired range.

To determine the biomass produced by any of the above mentioned fermentation methods, a known volume of broth is centrifuged and the supernatant is discarded. The pellet is resuspended in 30–40 ml cold saline. The resuspended solution is then centrifuged for 15-25 minutes at 10,000–15,000×g (4° C.). The supernatant is removed and discarded. This procedure is repeated with deionized water (at room temperature). The pellet is dried under vacuum at 80° C. for 24 hr. The dried pellet, which includes cellulose and cells, is weighed. Biomass is defined as mass (in grams) of dried cellulose and cells per volume of broth (in liters).

Cellulose produced by any of the above mentioned fermentation methods may be recovered from the fermentation broth using conventional harvesting techniques. In general, any method for separating the cellulose from the broth may be used, but centrifugation is preferred. Each batch of fermentation broth containing the cellulose producing microorganism, used medium, and cellulose, is centrifuged. If cellulose concentration is to be calculated, the volume of the supernatant medium must be determined. The supernatant is then discarded. The pellet comprising solid matter, including the microorganisms and cellulose, is retained. The pellet is washed several times with cold saline to remove residual medium. The retained matter is treated with an alkali solution such as 0.1M NaOH or KOH at 60° 14 65° C. The alkali treated material is subsequently centrifuged. The pellet is retained for cellulose measurements and the supernatant is used to determine cell concentration. The pellet is washed and centrifuged three or four times in deionized water, dried in a vacuum oven and weighed to determine cellulose mass. Cell concentration is estimated from the protein concentration in the supernatant, assuming cells with 65% protein.

In the various examples provided below, certain measurements are reported. The definitions immediately following describe how the measurement have been calculated.

Volumetric productivity is defined as total mass of cellulose produced per volume of medium used per fermentation time (g/L/hr), from inoculation to harvest for batch cultures.

Cellulose yield is defined as the change in cellulose concentration (g/L) divided by the substrate utilized (g/L). The amount of substrate utilized can be measured between any two time points.

The corrected yield is the cellulose yield which has been corrected for substrate and/or product which were added or removed during fermentation. A volume correction is also added into the calculation of corrected yield.

Cellulose yield corrected for these changes can be calculated using the following equation:

$$Y_n = \frac{P_n \cdot V_{F_n} + \sum_i^n V_{S_i} \cdot P_i - P_1 \cdot V_{F_1}}{V_1 \cdot S_1 + \sum_i^n G_i - \sum_i^n V_{S_i} \cdot S_i - S_n \cdot V_{F_n}}$$

where $$V_{F_n} = V_{F_1} + \sum_i^n V_{A_i} - \sum_i^n V_{S_i}$$

G = Glucose (g) added from $t_{i-1}$ to $t_i$
T = Time (h)
$V_F$ = Fermentor volume (L)
S = Glucose concentration (g/L)
P = Cellulose concentration (g/L)
$V_S$ = Sample volume (L) from time $t_{i-1}$ to $t_i$
$V_A$ = Liquid volume (L) from time $t_{i-1}$ to $t_i$ (glucose, base, and CSL)
Y = Cellulose Yield (g/g)

Polymers in their simplest form are large molecules that are assembled from repeating monomeric units where there can be thousands of monomeric units in a single polymer unit connected much like links in a chain. For example, the monomer acrylamide ($C_3H_5NO$) serves as the repeating unit of polyacrylamide $(C_3H_5NO)_n$ where n can be 10,000 per molecule or greater. In general, methods of measuring the molecular weight of polymers yield an average value. Those methods based on colligative properties of solutions, which, in effect, count the number of molecules in a known mass of material to give the number-average molecular weight, $\overline{M}_n$. $\overline{M}_n$ is defined by the equation $$M_n = \frac{\Sigma N_i M_i}{\Sigma N_i}$$

where $N_i$=the number of molecules of a particular weight, $M_i$. Other methods of molecular weight determination, such as light scattering, tend to measure the contribution of a molecule as a function of mass. These methods give the weight-average molecular weight, $\overline{M}_w$, as shown below:

$$M_w = \frac{\Sigma N_i M_i^2}{\Sigma N_i M_i}$$

The following examples are offered by way of illustration and are not intended to limit the invention in any manner. In these examples all percentages are by weight if for solids and by volume if for liquids, and all temperatures are in degrees Celsius unless otherwise noted.

In the following examples a number of culture media are mentioned. Unless otherwise indicated, the media are formulated as indicated below:

| R70-3 | |
|---|---|
| Ingredient | Final Concentration (mM) |
| $(NH_4)_2SO_4$ | 25 |
| $KH_2PO_4$ | 7.3 |
| Na Citrate | 4.0 |
| $MgSO_4$ | 1.0 |
| $FeCl_3$ | 0.05 |
| $CaCl_2$ | 0.10 |
| $Na_2MoO_4$ | 0.001 |
| $ZnSO_4$ | 0.005 |
| $MnSO_4$ | 0.005 |
| $CuSO_4$ | 0.001 |
| $CoCl_2$ | 0.001 |
| $NiCl_2$ | 0.001 |
| Vitamin mix (see below) | 10 ml/liter |
| Glucose as specified (usually 2 or 4%, w/v) | |
| final pH = 5.0 ± 0.2 | |

| Vitamin Mix | |
|---|---|
| Compound | mg/L in mix |
| Inositol | 200 |
| Niacin | 40 |
| Pyridoxine HCl | 40 |
| Thiamine HCl | 40 |
| Ca Pantothenate | 40 |
| Riboflavin | 20 |
| PaBa | 20 |
| Folic Acid | 0.2 |
| Biotin | 0.2 |

The composition of corn steep liquor varies depending on supplier and mode of treatment. A typical corn steep liquor sample, Type E804 obtained from Corn Products Unit, CPC North America, Stockton, Calif. is described below:

| Major Components | Percent |
|---|---|
| Solids | 43.8 |
| Crude protein | 18.4 |
| Fat | 0.5 |
| Crude fiber | 0.1 |
| Ash | 6.9 |
| Calcium | 0.02 |
| Phosphorous | 1.3 |
| Nitrogen free extract | 17.8 |
| Non-protein nitrogen | 1.4 |
| NaCl | 0.5 |
| Potassium | 1.8 |
| Reducing sugars (as dextrose) | 2.9 |
| Starch | 1.6 |
| pH | 4.5 |

EXAMPLE 1

Effects of Agitation in Flask Studies

This study examines whether different agitation conditions in flasks affect cell growth and cellulose production. The seed was grown in R70-3 media with 0.5% (w/v) Technical Grade Yeast Extract, Amberex 1003, Universal Foods (TYE), 30 g/L glucose, 25 mM 3,3 dimethylglutaric acid (DMG) and 0.1% (v/v) cellulase (Genencor). Cellulase was added to degrade the cellulose produced, thus allowing the cells to grow as single cell suspensions. For the production stage, the cellulase is diluted out to prevent interference with cellulose production. One frozen vial of Acetobacter strain 1306-21 was used to inoculate the seed (50 ml medium in a 250 ml baffled flask), which was then incubated overnight at 30° C., 125 rpm.

The base medium for the experiment was R70-3 with 2% (v/v) corn steep liquor (CSL), 10 g/L glucose and 25 mM DMG. Studies at 125 and 200 rpm used shakers that had a 2" throw. Studies at 375 rpm used a New Brunswick shaker with a 1" throw. Flasks were removed from the shakers at 1 and 3 days and analyzed for cells and cellulose.

Cell growth and cellulose production at day 3, which represents the end of cell growth and stationary phase (based on glucose consumption), are given in Table 1. The agitation conditions have a strong effect on the cellulose to cell ratio, and cellulose yield. After three days of incubation the cell growth was similar in the four systems tested (similar cell yield). The cellulose to cell ratios decreased by the following order: 125 rpm (non-baffled) > 125 rpm > 200 rpm > 375 rpm. The contribution of the CSL to cellulose production on 2% CSL alone is 0.48 g/L (cellulose production on 2% CSL, without glucose). Partial correction for CSL effect was made by omitting this value from cellulose results. Cellulose yield is high at low agitation (0.38 g/g) and low at high agitation (0.15 g/g). The order for cellulose yield values was: 125 rpm (non-baffled) > 125 rpm > 200 rpm > 375 rpm.

TABLE 1

Effect of Agitation on Cellulose Yield and Cell Growth Strain 1306-21 in R70-3 plus 2% CSL, 25 mM DMG and 1% glucose Day 3 Results

| | Cellulose (g/L) | Average Cellulose (g/L) | Cell Mass (g/L) | Cellulose/Cell Ratio (g/g) |
|---|---|---|---|---|
| 125 rpm Non-Baffled | 4.25 4.18 | 4.23 | 1.21 | 3.50 |
| 125 rpm Baffled | 3.58 3.66 | 3.62 | 1.15 | 3.15 |

TABLE 1-continued

Effect of Agitation on Cellulose Yield and Cell Growth Strain 1306-21 in R70-3 plus 2% CSL, 25 mM DMG and 1% glucose Day 3 Results

| | | | | |
|---|---|---|---|---|
| 200 rpm Baffled | 2.89 2.99 | 2.94 | 1.27 | 2.31 |
| 375 rpm Baffled | 2.06 1.89 | 1.98 | 1.34 | 1.48 |

| | Res. Glc (g/L) | Cellulose Yield (Uncorrected) (g/g) | Cellulose Yield (Corrected)[b] (g/g) |
|---|---|---|---|
| 125 rpm Non-Baffled | ND[a] | 0.42 | 0.38 |
| 125 rpm Baffled | ND | 0.36 | 0.31 |
| 200 rpm Baffled | ND | 0.29 | 0.25 |
| 375 rpm Baffled | ND | 0.20 | 0.15 |

[a]ND = Not Detectable (0.2 g/L)
[b]Assumes that 0.48 g/L cellulose was made from 2% CSL.

The 125 rpm non-baffled flasks grew as fairly large pellets (2-5 mm) on the 1st day which aggregated into a single large blob on 2nd day. The structure of the blob was a fairly loose aggregation of the smaller pellets, so perhaps nutrients in the medium could enter the blob through convection currents. The 125 rpm baffled flask produced smaller pellets of approximately 1-2 mm, but there were a few larger pellets. The pellets in the 200 rpm baffled flask were smaller, and appear to be less well defined. The 375 rpm had a few small pellets, but the majority of the material had a debris-like appearance (0.5-1 mm).

This study showed that the agitation conditions have very strong effect on cellulose production, cellulose to cell ratio, and cellulose yield. This system was used as described below to test the effect of protecting agents on pellet form, and the effect of shear on cellulose yield and productivity.

EXAMPLE 2

Initial Screen of Protectants

The studies described herein include a survey of potential protectants against shear stress and calibration of the most effective protectants.

Four separate experiments were run with 25 ml of medium in 125 ml baffled flasks. The base medium for all experiments was R70-3 plus 2% CSL, 10 g/L glucose and 25 mM DMG. Experiment B had 0.05% polypropylene glycol (antifoam), and Experiments C and D had 0.05 ml/L of Tween 80 to reduce growth on the walls of the flasks.

The seed procedure was followed as disclosed in Example 1.

The level of growth in each experiment was determined by biomass measurements which were done after the flasks had been incubated for three days at 30° C., 375 r (1" throw). This corresponds to the end of growth in a medium limited by glucose. The 125 rpm control flasks were incubated at 30° C. on shaker with a 2" throw.

For Experiment A, the protectants were either sterilized separately and added aseptically, or they were added to the medium which was then filter sterilized. For Experiments B, C, and D, the protectants were autoclaved with the medium. The appropriate amount of material was put in an empty milk dilution bottle and citrate, $KH_2PO_4$, $(NH_4)_2SO_4$, $MgSO_4$ and deionized $H_2O$ were added. The pH was adjusted to 5 with HCl, and the solutions were autoclaved. The vitamins, trace metals, CSL, DMG, and glucose were added aseptically. This approach was necessary because many of the substances tested in Experiments B, C and D would not filter sterilize at the concentrations tested.

The following substances were tested:

Agar (Meer Corporation Crude Flake Agar), 2 g/L autoclaved with medium.

Alginic Acid (Sigma), 1 g/L added to medium and filter sterilized for Experiment A. 1 and 5 g/L autoclaved with medium in Experiment B.

Alginsaure (Atomergic Chemetals Corp), 10% (w/v) solution autoclaved and added aseptically. Concentrations tested were 1 and 5 g/L. (Alginsaure is the German name for alginic acid).

Carbopol 934P (B. F. Goodrich), 1 and 3 g/L autoclaved with medium.

Carboxymethyl Cellulose (Sigma), 1 and 5 g/L autoclaved with medium.

Gum Guar (Sigma), 1 and 5 g/L autoclaved with medium.

Gum Xanthan (Sigma), 1 and 5 g/l autoclaved with medium.

Gummi Arabicum (Atomergic Chemetal Corp), 1 and 5 g/L autoclaved with medium.

Indulin AT (Westvaco Chemical), 10% (w/v) solution autoclaved and added aseptically. Concentrations tested were 1 and 5 g/L. (Indulin AT is a lignin polymer).

Maltose (Sigma), 1 and 5 g/L added to medium and filter sterilized.

Methyl Cellulose, 10% Stock solution autoclaved and added aseptically. Concentrations tested were 1 and 5 g/L.

Pectinic Acid (Atomergic Chemetals), 1 and 5 g/L autoclaved with medium.

Pluronic, 10% (w/v) stock solution was filter sterilized and added aseptically. Concentrations tested were 1 and 5 g/L.

Polyethylene Glycol, 6000 MW (BDH Chemicals), added to medium and filter sterilized. Concentrations tested were 1 and 5 g/L.

Poly(ethylene oxide) MW 100,000 (Aldrich), 0.3 and 3.0 g/L autoclaved with medium.

Polygalacturonsaure (Atomergic Chemetals), 1 and 5 g/L autoclaved with medium. (Polygalacturonsaure is the German name for polygalacturonic acid).

Polyvinyl Alcohol type II (Sigma), added to medium and filter sterilized. Concentrations tested were 1 and 5 g/L.

Potato Starch (Kalamazoo Paper Chemicals), 1 and 5 g/L autoclaved with medium.

Potato Protein (Kalamazoo Paper Chemicals), 1 and 5 g/L autoclaved with medium.

Reten ® 210 (Hercules, Inc.), 0.1 and 1.0 g/L autoclaved with medium. (Reten ® 210 is a cationic copolymer of acrylamide and a quaternary ammonium monomer salt).

Reten ® 420 (Hercules, Inc.), 0.1 and 1.0 g/L autoclaved with medium. (Reten ® 420 is a nonionic polyacrylamide).

Reten ® 423 (Hercules, Inc.), 0.1 and 1.0 g/L autoclaved with medium. (Reten ® 423 is an anionic copolymer of sodium acrylate and acrylamide).

Traganth (Atomergic Chemetals Corp.), 1 and 5 g/L autoclaved with medium (Traganth is the German name for tragacanth gum).

Tween 80 (Sigma), filter sterilized and added aseptically (0.05–5 ml/L).

Whey (Sheffield), 1 and 5 g/L autoclaved with medium.

Xylan (Sigma), 1 and 5 g/L autoclaved with medium.

In the four experiments, the 375 rpm control biomass values were very consistent (the range was 2.96 to 3.13 g/L). The 125 rpm control flasks usually had values around 4.8–5.0 g/L, but Experiment B only had 4.34 g/L. The interference of insoluble medium components on the biomass values was determined for some of the systems. Sterile medium was centrifuged, and the pellet was washed and dried in the vacuum oven. The weight of the material was subtracted from the weight of the biomass. This value is referred to as the corrected biomass value.

Table 2 is a summary table of all four experiments.

The final pH of the 5 g/L alginsaure and the 3 g/L carbopol flasks was 4.2 and 4.5 respectively. The final pH in all of the other flasks was in the range of 4.7–5.2. Thus, pH did not appear to be a significant factor in any of the experiments.

Table 2 shows that the Reten ® polyacrylamides and xanthan gum gave the highest levels of stimulation. Reten ® 423 and Reten ® 420 gave the highest levels of biomass production (the biomass values were similar to the 125 rpm control values).

TABLE 2

Summary of Screen of Protectants
R70-3 plus 2% CSL and 10 g/L Glucose
Day 3 Results at 375 rpm

|  | Biomass (g/L) | Experiment |
|---|---|---|
| HIGHEST STIMULATION | | |
| *1 g/L Reten ® 423 | 5.05 | C |
| *1 g/L Reten ® 420 | 4.85 | C |
| MODERATE STIMULATION | | |
| *5 g/L Xanthan gum | 4.54 | B |
| *1 g/L Reten ® 210 | 4.47 | C |
| MARGINAL STIMULATION | | |
| *5 g/L Traganth | 3.97 | D |
| *5 g/L Xylan | 3.97 | B |
| *5 g/L Guar Gum | 3.84 | C |
| *1 g/L Indulin AT | 3.82 | A |
| *5 g/L Potato Starch | 3.81 | D |
| 3 g/L Carbopol | 3.78 | C |
| *2 g/L Agar | 3.63 | D |
| 1 g/L Methyl Cellulose | 3.63 | A |
| 5 g/L PEG (6000 MW) | 3.57 | A |
| NO STIMULATION (<3.5 g/L) | | |
| 1,5 g/L Pluronic | | A |
| 1,5 g/L Alginic Acid | | B |
| 1,5 g/L Pectinic Acid | | D |
| 0.1, 10 ml/L Tween 80 | | A |
| 1,5 g/L Polyvinyl Alcohol | | A |
| 1,5 g/L Alginsaure | | A |
| 1,5 g/L Polygalacturonsaure | | D |
| 1,5 g/L Maltose | | D |
| 1,5 g/L Carboxy Methyl Cellulose | | B |
| 1,5 g/L Gummi Arabicum | | B |
| 1,5 g/L Whey | | C |
| 0.3, 3 g/L Polyethylene oxide | | C |
| 0.1, 1, 5 g/L Colloidal Chitin | | C |

|  | A | B | C | D |
|---|---|---|---|---|
| 125 rpm Control Values - | 5.03 | 4.34 | 4.82 | 4.92 |
| 375 rpm Control Values - | 3.13 | 3.10 | 2.96 | 3.06 |

*Biomass Value corrected for precipitate derived from the protectant.

EXAMPLE 3

Additional Screen for Protectants

The studies described herein include an additional survey of polyacrylamide protectants (Experiment A) and a calibration of the most effective protectants from this survey (Experiment B).

Both sets of experiments were done in 125 ml baffled flasks which were incubated at 30° C. and agitated at 375 rpm (1″ throw).

The medium was R70-3 plus 2% (v/v) CSL, 10 g/L glucose, 25 mM DMG and 0.05% (v/v) Tween 80. The individual components were weighed into bottles and solutions of the major salts were added (citrate, $KH_2PO_4$, $MgSO_4$, $(NH_4)_2SO_4$). The solutions were autoclaved for 20 min. and then the other components were added aseptically (CSL, DMG, trace salts, vitamins, Tween 80, glucose). The Tween 80 was present in the medium to help prevent wall growth in the flasks. The medium was then dispensed to 125 ml baffled flasks.

The seed procedure was followed as disclosed in Example 1.

The strain 1306-21 was used for both experiments. The seed flask was inoculated with a frozen vial of 1306-21 and incubated overnight at 30° C., 125 rpm (2″ throw). The seed medium was R70-3 plus 0.5% (w/v) TYE, 30 g/L glucose, 25 mM DMG and 0.1% (v/v) cellulase (Genencor). Each test flask received a 5% inoculum. The flasks were incubated for three days at 30° C., 375 rpm (1″ throw). The level of glucose was measured using a Yellow Spring Instrument (YSI) on the third day, and all of the flasks had 0.1 g/L glucose or less.

All polyacrylamides were tested at a concentration of 0.4 g/L in Experiment A. In Experiment B, the calibration study, the most promising of the polyacrylamide protectants from Experiment A were tested at 0.2, 0.4 and 1.0 g/L in order to estimate the most effective concentration.

The results of Experiment A are shown in Table 3.

TABLE 3

Survey of Protectants on Biomass Production in 1306-21
in R70-3 plus 2% CSL, 10 g/L Glucose, 0.05% Tween 80 and
Polyacrylamide Protectant (0.4 g/L) Day 3 Results at 375 ppm

|  | Biomass (g/L) |
|---|---|
| 125 rpm Control | 5.68 |
| 375 rpm Control | 3.27 |
| Anionic Polyacrylamides: | |
| Reten ® 423 | 5.51 |
| Magnifloc ® 833A | 5.90 |
| Aldrich Polyacrylamide (Carboxyl Modified, Low) | 3.77 |
| Aldrich Polyacrylamide (Carboxyl Modified, High) | 3.60 |
| Cyanamer ® P-35 | 3.56 |
| Cyanamer ® P-21 | 3.71 |
| Cyanamer ® A-370 | 3.51 |
| Nonionic Polyacrylamides: | |
| Reten ® 420 | 4.66 |
| Magnifloc ® 985N* | 4.75 |
| Cyanamer ® N-300 | 4.79 |
| Aldrich Polyacrylamide | 4.75 |

*Single Flask

Table 3 shows that of the anionic polyacrylamides tested, Reten ® 423 and Magnifloc ® 833A enhanced biomass production to the greatest extent. Of the nonionic polyacrylamides tested, Reten ® 420, Magnifloc ® 985N, Cyanamer ® N-300 and Aldrich nonionic polyacrylamide all enhanced biomass production.

The results of Experiment B, the calibration experiment, are shown below.

TABLE 4

Calibration of Protectants on Biomass Production in 1306-21 in R70-3 plus 27% CSL, 10 g/L Glucose, 0.05% Tween 80 and Polyacrylamide Protectant Day 3 Results at 375 rpm

|  | Biomass (g/L) |
| --- | --- |
| 125 rpm Control | 5.87 |
| 375 rpm Control | 3.77 |
| Anionic Polyacrylamides: | |
| Polytec 36 | |
| (0.2 g/L) | 5.35 |
| (0.4 g/L) | 5.70 |
| (1.0 g/L) | 6.79 |
| Magnifloc ® 833A | |
| (0.2 g/L) | 5.22 |
| (0.4 g/L)* | 4.77 |
| (1.0 g/L) | 6.47 |
| Nonionic Polyacrylamides: | |
| Reten ® 420 | |
| (0.2 g/L) | 4.32 |
| (0.4 g/L) | 4.85 |
| (1.0 g/L) | 5.39 |
| Polytec 31 | |
| (0.2 g/L) | 4.45 |
| (0.4 g/L) | 4.95 |

TABLE 4-continued

Calibration of Protectants on Biomass Production in 1306-21 in R70-3 plus 27% CSL, 10 g/L Glucose, 0.05% Tween 80 and Polyacrylamide Protectant Day 3 Results at 375 rpm

|  | Biomass (g/L) |
| --- | --- |
| (1.0 g/L) | 5.50 |
| Magnifloc ® 985N | |
| (0.2 g/L) | 4.32 |
| (0.4 g/L)* | 4.49 |
| (1.0 g/L) | 5.50 |
| Cyanamer ® N-300 | |
| (0.2 g/L) | 4.39 |
| (0.4 g/L)* | 4.62 |
| (1.0 g/L) | 5.26 |

*Medium was stored for approximately 35 days, with protectant in it.

As the data in Table 4 illustrate, the preferred concentration for the polyacrylamide protectants in flask cultures appears to be close to 1 g/L. Further, Polytec 31 and Polytec 36 are also effective as protectants.

Yet additional screening assays were performed. The results of all of the screening assays, in which various protectants were tested at 0.4 g/L are compiled in Table 5. The biomass values are expressed as a percentage of the biomass measurement of the 125 rpm control. Multiple biomass values for one protectant indicates that multiple experiments were performed.

TABLE 5

Comparison of Protectants: Effect on Biomass Production, Ionic Classification, Molecular Weight

| Protectant | Biomass (%) | Polyacrylamide[a] | M. Wt[b] | Company |
| --- | --- | --- | --- | --- |
| None | 61–58 | | | |
| Reten ® 420 | 89–82, 89–85 | Nonionic | High | Hercules |
| Polytec 31 | 91 | Nonionic | $5.1 \times 10^6$ | Tecna |
| Polyacrylamide | 84 | Nonionic | $(5-10) \times 10^6$ | Aldrich |
| Magnifloc ® 985N | 84 | Nonionic | Ultra High | Cyanamid |
| Cyanamer ® N300 LMW | 90–84 | Nonionic | $5 \times 10^6$ | Cyanamid |
| Reten ® 423 | 102–97 | Moderate Anionic (—COONa) | High | Hercules |
| Polyacrylamide | 66 | Low Anionic (COO—) | $2 \times 10^5$ | Aldrich |
| Polyacrylamide | 63 | High Anionic (COO—) | $2 \times 10^5$ | Aldrich |
| Cyanamer ® P-21 | 68–65 | 10% Anionic (COO—) | $2 \times 10^5$ | Cyanamid |
| Cyanamer ® A-370 | 64–62 | 90% Anionic (COO—) | $2 \times 10^5$ | Cyanamid |
| Polytec 36 | 105 | 20–30 mole % Anionic (Na) | $6.5 \times 10^6$ | Tecna |
| Magnifloc ® 833A | 104 | Anionic | $5.5 \times 10^6$ | Cyanamid |
| Cyanamer ® P-35 | 61–63 | very high anionic Modified | $10^4$ | Cyanamid |
| Floxan ® EA 1340 | 93—93 | Medium Anionic (24% kerosene) | $5.6 \times 10^6$ | Henkel |
| Reten ® 210 | ND | Medium Cationic | $4.9 \times 10^6$ | Hercules |
| Floxan ® SC-5062 | 61 | High Cationic | Low | Henkel |
| Floxan ® SC-5067 | 65 | High Cationic | Low | Henkel |
| Floxan ® SC-5080 | 66 | High Cationic | Low | Henkel |

TABLE 5-continued

Comparison of Protectants: Effect on Biomass Production, Ionic Classification, Molecular Weight

| Protectant | Biomass (%) | Polyacrylamide[a] | M. Wt[b] | Company |
|---|---|---|---|---|
| Floxan ® SC-5082 | 57 | High Cationic | Low | Henkel |
| Floxan ® EC-2000 | 84–72 | Low Cationic (24% kerosene) | $4.6 \times 10^6$ | Henkel |

[a]Ionic classification is based on manufacture's specifications.
[b]Molecular weight is based either on manufacturer's specifications or our own measurements for weight average molecular weight.

The nonionic polyacrylamides generally appear to be good protectants. Fermentations run in the presence of nonionic polyacrylamides and agitated at 375 rpm generally had biomass concentrations from 82–91% of the biomass concentration of the 125 rpm control. Fermentations run without protectant and agitated at 375 rpm had biomass concentrations of only 58–61% of the biomass concentration of the 125 rpm control.

There was substantial variation in the ability of anionic polyacrylamides to increase biomass production at high agitation rates. Fermentations run in the presence of anionic polyacrylamides had biomass concentrations ranging from 62–105% of the biomass concentration of the 125 rpm control fermentation.

In general, high molecular weight polymers appear to be better protectants. In addition, low molecular weight cationic polyacrylamides with high and medium cationic charge are generally not good protectants.

EXAMPLE 4

Effects of Polyacrylamide Protectants in High Density Fermentation

Experiment A

Reten ® 420 and Reten ® 423 were previously shown to increase biomass production when added to flask fermentations of Acetobacter. This study was designed to investigate whether cellulose yields could be increased by use of these polyacrylamides in high density fermentation.

The medium used to grow the pre seed and seed was R70-3 with 0.5% (w/v) TYE, 3% (w/v) glucose, 25 mM DMG, 0.05% antifoam (polypropylene glycol) and 0.10% (v/v) cellulase (Genencor). For each 2000 ml flask, 350 ml medium was used.

For the pre-seed, one flask was inoculated with 1 frozen vial (approximately 1.8 ml) of stock. The flask was incubated at 30° C., 125 rpm in a 2" throw incubator for 1 day.

For the seed, each flask was inoculated with 35 ml of the pre seed culture and incubated at 30° C., 125 rpm for 1 day. The seed cultures had $OD_{680}$ measurements of 1.5–2.

The medium for the fermentor runs was R70-3 plus 3% glucose, and 4% (v/v) CSL. The CSL was titrated to pH 5.0 with NaOH and centrifuged to remove insolubles before use. The $(NH_4)_2SO_4$ initial concentration was 12.5 mM. Glucose, vitamins, and trace elements were sterilized separately. Protectants, when added, were sterilized with the medium. The glucose and ammonia concentrations were kept in excess throughout the run by addition during the fermentation. The pH was controlled at 5.0 by automatic addition of 4N $H_2SO_4$ or 4N $NH_4OH$. Glucose addition was coupled to the base demand using an approximate ratio of 1 g glucose to 1.2 mmole base.

The inoculum used was approximately 4% (v/v).

The fermentors used were 14 L Chemap fermentors equipped with Rushton impellers. The temperature was controlled at 30° C. The dissolved oxygen concentration was controlled at 60% of air saturation. The agitation was manually controlled to provide adequate mixing and ranged from 600 rpm initially to 1,200 rpm toward the end of the run. Aeration was controlled by demand with oxygen enriched air.

In the fermentors containing protectant, 1 g/L of either Reten ® 420 or Reten ® 423 was added before sterilization. Sterilization time was 45 minutes.

Table 6 summarizes the results from this study.

TABLE 6

Effect of Reten ® 420 and Reten ® 423 in the Fermentation Medium Strain 1306-21 in R70-3 plus 4% CSL

| | Run Time (hr.) | Cellulose (g/L) | Cells (g/L) | Cellulose Yield (g/g) | Volumetric Productivity (g/L-hr) |
|---|---|---|---|---|---|
| Control | 0.00 | | 0.02 | | |
| | 10.28 | 0.17 | 0.27 | | 0.02 |
| | 20.46 | 0.95 | 1.11 | | 0.05 |
| | 24.23 | 1.89 | 1.66 | 0.28 | 0.08 |
| | 28.72 | 3.18 | 2.51 | 0.25 | 0.11 |
| | 34.26 | 5.21 | 3.83 | 0.22 | 0.15 |
| | 44.94 | 10.77 | 7.05 | 0.20 | 0.24 |
| | 50.36 | 13.14 | 7.94 | 0.19 | 0.26 |
| | 59.10 | 17.64 | 11.57 | 0.17 | 0.30 |
| 1 g/L Reten ® 420 | 0.00 | | 0.02 | | |
| | 10.16 | 0.30 | 0.28 | 0.21 | 0.03 |
| | 20.37 | 1.93 | 1.32 | 0.51 | 0.09 |
| | 24.21 | 3.33 | 1.76 | 0.34 | 0.14 |
| | 28.52 | 4.60 | 2.94 | 0.25 | 0.16 |
| | 34.16 | 8.34 | 4.94 | 0.24 | 0.24 |
| | 45.16 | 16.12 | 10.02 | 0.20 | 0.36 |
| 1 g/L Reten ® 423 | 0.00 | | 0.02 | | |
| | 10.21 | 0.30 | 0.27 | 0.30 | 0.03 |
| | 20.41 | 1.76 | 1.15 | 0.49 | 0.09 |
| | 24.22 | 2.96 | 1.64 | 0.37 | 0.12 |
| | 28.68 | 3.88 | 2.38 | 0.25 | 0.14 |
| | 34.18 | 6.86 | 4.08 | 0.27 | 0.20 |
| | 44.73 | 12.17 | 5.71 | 0.23 | 0.27 |
| | 50.21 | 15.25 | 7.59 | 0.22 | 0.30 |
| | 58.94 | 20.54 | 10.39 | 0.20 | 0.35 |

Addition of the polyacrylamides Reten ® 420 and Reten ® 423 to the fermentation medium increased cellulose yield and volumetric productivity.

Both of the Reten ® runs had final cellulose yields of 0.20 g/g. This value is slightly higher than the control run. Yields from the Reten ® runs, at intermediate concentrations of cellulose, were higher than the yield from the control run. The 1 g/L Reten ® 420 run had a yield of 0.24–0.25 g/g up to 8.3 g/L cellulose before it dropped to 0.20 g/g. The 1 g/L Reten ® 423 run had a yield of 0.27 g/g at 6.9 g/L cellulose. Cellulose volumetric productivity at the end of these runs was 0.30 g/L hr in the control and 0.36 g/L hr with Reten ® 420 and Reten ® 423.

Experiment B

This experiment was designed to assess the effect of Magnifloc ® 833A, Polytec 31 and Polytec 36 on cellulose production in high density fermentation. The medium and seed preparation were the same as that disclosed in Experiment A. The polyacrylamides were tested at a concentration of 1 g/L. Each was added to the respective fermentor before sterilization.

The CSL was added to the fermentors after the protectants. The broth was then sterilized according to the standard protocol.

The results are summarized in Table 7.

TABLE 7

Effects of Magnifloc ® 833A, Polytec 31 and Polytec 36 in the Fermentation Medium Strain 1306-21 in R70-3 plus 4% CSL

| Run Time (hrs.) | Agitation (rpm) | Cellulose (g/L) | Cells (g/L) | Yield (g/g) | Vol. Prod. (g/L-hr) |
|---|---|---|---|---|---|
| 1 g/L Magnifloc ® 833A | | | | | |
| 0.00 | 600 | | 0.03 | | |
| 9.48 | 600 | 0.24 | 0.28 | | 0.03 |
| 21.35 | 600 | 1.79 | 1.19 | 0.43 | 0.08 |
| 25.01 | 600 | 2.69 | 1.65 | 0.25 | 0.11 |
| 28.92 | 600 | 3.71 | 2.24 | 0.24 | 0.13 |
| 34.92 | 650 | 7.78 | 3.52 | 0.27 | 0.22 |
| 44.76 | 750 | 13.43 | 4.79 | 0.26 | 0.30 |
| 51.43 | 750 | 16.44 | 6.96 | 0.22 | 0.32 |
| 1 g/L Polytec 31 | | | | | |
| 0.00 | 600 | | 0.03 | | |
| 9.52 | 600 | 0.30 | 0.29 | | 0.03 |
| 21.38 | 600 | 2.49 | 1.23 | 0.44 | 0.12 |
| 25.03 | 600 | 4.04 | 1.92 | 0.43 | 0.16 |
| 28.94 | 600 → 800 | 5.47 | 3.01 | 0.27 | 0.19 |
| 34.96 | 800 → 900 | 10.43 | 4.61 | 0.26 | 0.30 |
| 44.81 | 1200 | 15.13 | 7.92 | 0.21 | 0.34 |
| 51.50 | 1200 | 16.24 | 8.49 | 0.19 | 0.32 |
| 1 g/L Polytec 36 | | | | | |
| 0.00 | 600 | | 0.03 | | |
| 9.56 | 600 | 0.19 | 0.30 | | 0.02 |
| 21.42 | 600 | 2.45 | 1.34 | 0.35 | 0.11 |
| 25.08 | 600 | 3.79 | 1.92 | 0.37 | 0.15 |
| 29.01 | 600 → 750 | 5.61 | 2.74 | 0.29 | 0.19 |
| 35.03 | 750 → 900 | 10.36 | 4.06 | 0.28 | 0.30 |
| 44.87 | 1200 | 14.72 | 6.87 | 0.23 | 0.33 |
| 51.57 | 1120 | 16.28 | 8.08 | 0.20 | 0.32 |

Control values are provided in Table 6

Addition of the polyacrylamides Magnifloc ® 833A, Polytec 31 and Polytec 36 to the fermentation medium increased cellulose yield at high concentrations of cellulose. For control run see Table 6. The agitation protocol used for the control run was similar to the one used with Polytec 31 and Polytec 36. Cellulose volumetric productivity was higher in each of the fermentors containing a polyacrylamide than in the control fermentor, which lacked polyacrylamide. Addition of Magnifloc ® 833A also improved the mixing properties of the broth, as evidenced by the ability to maintain effective mixing at lower rpm's. Further studies with Magnifloc ® 833A showed that the results with respect to cellulose yield and productivity can vary (see Table 9).

EXAMPLE 5

Effect of Floxan ® EA-1340 on Cellulose Production in High Density Fermentation

In this study, the effect of various concentrations of the polyacrylamide protectant Floxan ® EA-1340 on cellulose production in high density fermentation was examined. Floxan ® EA-1340 is an anionic polyacrylamide in oil water emulsion.

A standard cellulose pre seed and seed of 1306-21 were grown for these fermentations. Standard fermentation medium was also used.

The Floxan ® EA-1340 was tested at concentrations of approximately 0.5, 1, and 3 g/L and was added to each fermentor before sterilization. In the test runs containing Floxan ® EA-1340 at concentrations of 0.5 and 1 g/L, the Floxan ® was added to room temperature medium. In the test run containing 3 g/L Floxan ® EA-1340, the polyacrylamide was added after the medium was heated to 40° C.

PPG antifoam (5 ml) was added to the 0.5 g/L and 3 g/L Floxan ® runs before sterilization. 10 ml of Dow B antifoam was added to all 3 fermentors at 11.4 hours. Table 8 summarizes the results from all of the runs.

TABLE 8

Calibration of Floxan ® EA-1340 in the Fermentation Medium Strain 1306-21 in R70-3 plus 4% CSL

| Run Time (hr.) | Agitation (rpm) | Cellulose (g/L) | Cells (g/L) | Cellulose Yield. (g/g) | Corr. Yield (g/g) | Vol. Prod. (g/L-Hr) |
|---|---|---|---|---|---|---|
| Control | | | | | | |
| 0.00 | 600 | | 0.02 | | | |
| 10.28 | 600 | 0.17 | 0.27 | | | 0.02 |
| 20.46 | 600 | 0.95 | 1.11 | | | 0.05 |
| 24.23 | 600 | 1.89 | 1.66 | 0.28 | 0.31 | 0.08 |
| 28.72 | 600 | 3.18 | 2.51 | 0.25 | 0.27 | 0.11 |
| 34.26 | 750 | 5.21 | 3.83 | 0.22 | 0.23 | 0.15 |
| 44.94 | 950 | 10.77 | 7.05 | 0.20 | 0.22 | 0.24 |
| 50.36 | 950 | 13.14 | 7.94 | 0.19 | 0.21 | 0.26 |
| 59.10 | 1100 | 17.64 | 11.57 | 0.17 | 0.20 | 0.30 |
| 0.5 g/L Floxan ® EA-1340 | | | | | | |
| 0.00 | 600 | | 0.03 | | | |
| 10.60 | 600 | 0.21 | 0.28 | | | 0.02 |
| 20.90 | 600 | 1.66 | 1.19 | 0.27 | 0.30 | 0.08 |
| 25.21 | 600 | 3.03 | 1.85 | 0.25 | 0.26 | 0.12 |
| 29.29 | 600 → 700 | 4.80 | 2.50 | 0.24 | 0.26 | 0.16 |
| 34.27 | 700 → 850 | 8.11 | 3.84 | 0.24 | 0.25 | 0.24 |
| 44.59 | 850 → 1000 | 16.79 | 6.95 | 0.24 | 0.26 | 0.38 |
| 52.12 | 1200 | 18.39 | 9.09 | 0.18 | 0.22 | 0.35 |
| 1 g/L Floxan ® EA-1340 | | | | | | |
| 0.00 | 600 | | 0.03 | | | |
| 9.85 | 600 | 0.31 | 0.26 | | | 0.03 |
| 21.72 | 600 | 2.25 | 1.29 | 0.24 | 0.26 | 0.10 |
| 25.30 | 600 | 3.57 | 1.88 | 0.26 | 0.28 | 0.14 |
| 29.62 | 700 → 800 | 6.10 | 2.82 | 0.26 | 0.27 | 0.21 |
| 35.17 | 1000 | 11.78 | 4.42 | 0.28 | 0.30 | 0.33 |
| 45.16 | 1100 | 16.48 | 6.45 | 0.21 | 0.25 | 0.36 |
| 3 ml/L Floxan ® EA-1340 | | | | | | |
| 0.00 | 600 | | 0.03 | | | |
| 10.60 | 600 | 0.37 | 0.21 | | | 0.03 |
| 20.90 | 600 | 2.06 | 0.99 | | | 0.10 |
| 25.22 | 600 → 700 | 3.84 | 1.60 | 0.38 | 0.40 | 0.15 |
| 29.29 | 700 → 900 | 5.91 | 2.32 | 0.31 | 0.33 | 0.20 |
| 34.31 | 900 → 1050 | 8.82 | 3.03 | 0.28 | 0.31 | 0.26 |
| 44.56 | 1050 → 1250 | 14.98 | 5.60 | 0.25 | 0.28 | 0.34 |
| 52.13 | 1250 | 15.00 | 5.96 | 0.22 | 0.24 | 0.29 |

Figure 1:
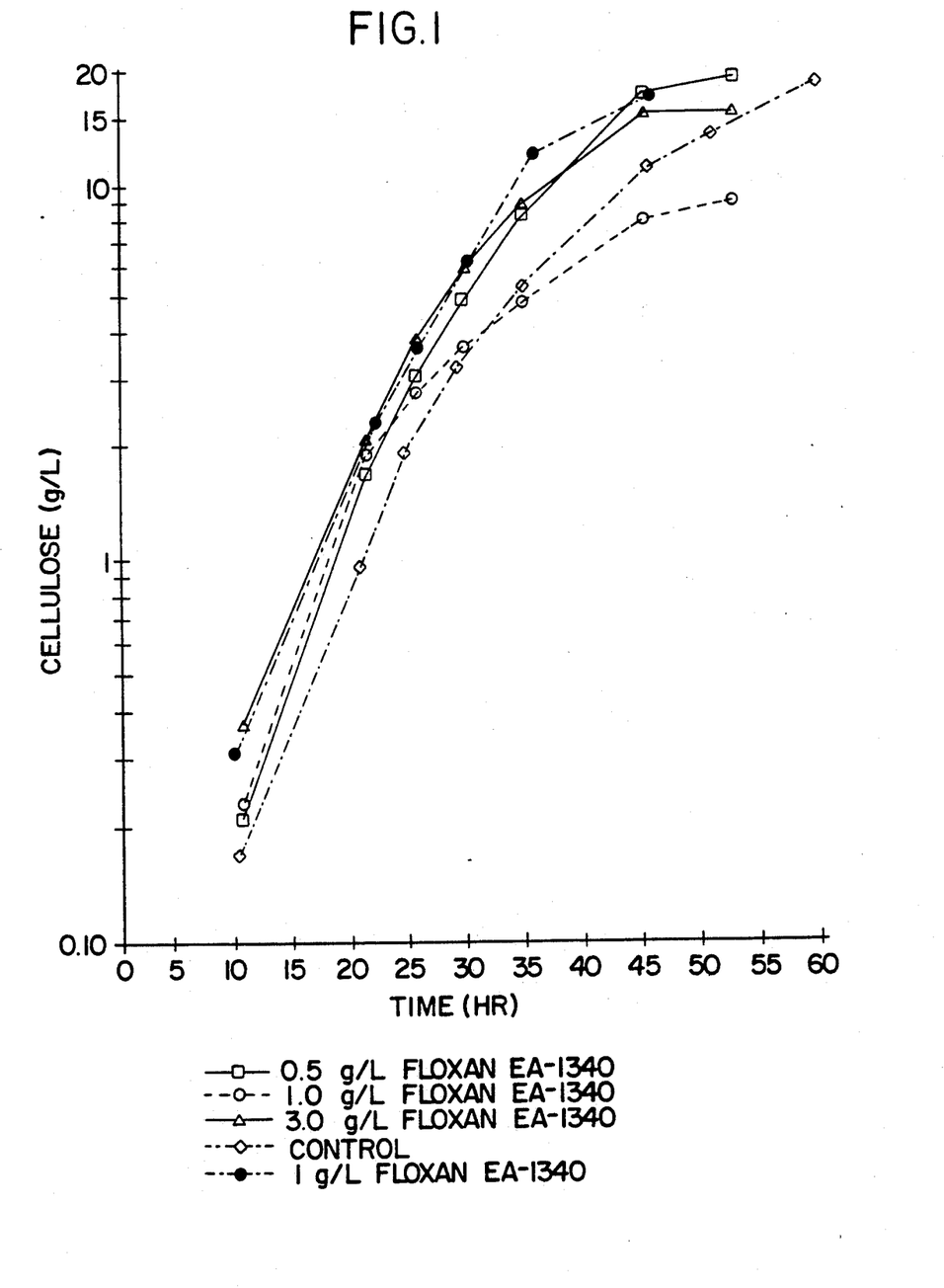
FIG. 1 is a graph which shows cellulose concentration versus time for fermentations run in the presence of various concentrations of the polyacrylamide Floxan ® EA-1340.

FIG. 1 shows cellulose concentration versus time for fermentations run in the presence of various concentrations of Floxan ® EA-1340. As shown in Table 8 and in FIG. 1, the addition of Floxan ® EA-1340 at 0.5, 1.0, and 3 g/L increased the cellulose yield at moderate and high cellulose concentrations. Cellulose volumetric productivity with 0.5 and 1.0 g/L Floxan ® EA-1340 was significantly higher than the control without Floxan ® EA-1340. At concentrations of Floxan ® EA-1340 of approximately 3 g/L, severe mixing problems occur late in the fermentor run. Approximately 1.0 g/L Floxan® EA-1340 appears to be an optimum concentration because at this concentration cellulose yield and volumetric productivity are enhanced, while prohibitive mixing problems are avoided.

Table 9 provides a compilation of the data for all the protectants tested in Chemap fermentors. Comparison has been made at various concentrations, in mixtures, or using different sterilization procedures, i.e., CSL was sterilized separately from the protectant. The volumetric productivity was calculated assuming 1 g/L initial cell concentration. This was done to normalize the results of the various runs to the same inoculum size.

TABLE 9

Effect of Protectants on Cellulose Production In High Density Fermentation

| Protectant | Conc. (g/L) | Cellulose Yield (g/g) Uncorrected Final | Vol. Prod. (g/L-hr) Final | Cellulose Conc. (g/g) |
|---|---|---|---|---|
| None | — | 0.17 | 0.43 | 17.6 |
| None | | 0.16 | 0.49 | 20.2 |
| Xanthan | 3.0 | 0.15 | 0.31 | 17.2 |
| Reten® 423 | 1.0 | 0.23 | 0.56 | 17.8 |
| Reten® 423 | 1.0 | 0.20 | 0.52 | 20.5 |
| Polytec 36 | 1.0 | 0.20 | 0.50 | 16.3 |
| Reten® 420 | 1.0 | 0.20 | 0.61 | 16.1 |
| Polytec 31 | 1.0 | 0.19 | 0.52 | 16.2 |
| Polytec 31 | 0.50 | 0.21 | 0.47 | 23.8 |
| Magnifloc® 833A | 1.0 | 0.22 | 0.52 | 16.4 |
| Magnifloc® 833A | 0.3 | 0.12 | 0.27 | 15.2 |
| Magnifloc® 833A | 3.0 | 0.21 | 0.22 | 11.0 |
| Magnifloc® 833A | 1.0 | 0.16 | 0.45 | 18.6 |
| Cyanamer P-21 | 1.0 | 0.19 | 0.46 | 14.4 |
| Magnifloc® 985N | 1.0 | 0.17 | 0.49 | 16.5 |
| Floxan® EA-1340 | 0.5 | 0.24 | 0.62 | 16.8 |
| Floxan® EA-1340 | 1.0 | 0.21 | 0.59 | 16.5 |
| Floxan® EA-1340 | 1.0 | 0.23 | 0.39 | 17.0 |
| Floxan® EA-1340 (CSL added as sterile addition) | 1.0 | 0.29 | 0.57 | 17.1 |
| Floxan® EA-1340 | 3.0 | 0.25 | 0.55 | 15.0 |
| Magnifloc® 833A + Floxan® EA-1340 | 0.3 1.0 | 0.20 | 0.50 | 18.5 |
| Floxan® EA-1340 + Magnifloc® 833A | 1.0 1.0 | 0.17 | 0.35 | 19.3 |
| Floxan® EC-2000 | 1.0 | 0.22 | 0.54 | 15.7 |

Reten® 423, Polytec 36, Reten® 420, Polytec 31, and Floxan® EC-2000 appeared to enhance cellulose yield and productivity. The effect of Magnifloc® 833A on cellulose yield and productivity varies. The consistent effect with this protectant is the improvement in the mixing properties of the broth. Cyanamer® P-21 and Magnifloc® 985N have no significant effect on cellulose yield and productivity. Floxan® EA-1340 gave the best results with respect to cellulose yield and productivity. Sterilization of the Floxan polyacrylamide separately from the CSL enhances cellulose yield (described in Example 7). Mixtures of Floxan® EA-1340 and Magnifloc® 833A polyacrylamides did not increase cellulose yield and productivity to the levels obtained with Floxan® EA-1340 polyacrylamide alone. However, the mixing properties with these mixtures of protectants were improved over that of the Floxan® EA-1340 polyacrylamide alone. In general, the results in the fermentor tests were consistent with the results in the flask screen (see Table 5) and affirm the relevance of the flask screening tests.

EXAMPLE 6

Analysis of Polyacrylamides

The concentration of polyacrylamides, nonionic, anionic and cationic, were measured by size exclusion chromatography using a 7.6×300 mm TSK-sized column packed with G6000PW-G3000PW 17 um beads. About 50 ul samples were injected onto the column and eluted at 1.0 mL/min with 0.2M $Na_2SO_4$. Detection was by UV absorbance at 200 nm.

The data presented in Table 10 indicates that a significant reduction in the weight-average molecular weight and the number average molecular weight of polyacrylamides occur after sterilization in the presence of the major salts of the R70-3 medium plus 4% CSL. No reduction in the weight average molecular weight or number average molecular weight of Floxan® EA-1340 was observed during sterilization in water at pH 5.0.

TABLE 10

The Effect of Sterilization on the Molecular Weight of Polyacrylamides

| Polyacrylamide | | Weight-Average M. Wt. | Number-Average M. Wt. |
|---|---|---|---|
| Polytec 31 | Before Sterilization | $5.1 \times 10^6$ | $2.2 \times 10^6$ |
| | After Sterilization* | $1.9 \times 10^6$ | $4.3 \times 10^5$ |
| Polytec 36 | Before Sterilization | $6.5 \times 10^6$ | $3.9 \times 10^6$ |
| | After Sterilization* | $1.6 \times 10^6$ | $4.2 \times 10^5$ |
| Floxan® EA-1340 | Before Sterilization | $5.6 \times 10^6$ | $2.5 \times 10^6$ |
| | After Sterilization* | $1.9 \times 10^6$ | $5.4 \times 10^5$ |

*The polyacrylamides were sterilized in the fermentors in the presence of the major salts of R70-3 medium and 4% CSL. The sterilization procedure is described in Example 4.

EXAMPLE 7

Effect of Medium Age, Age of Floxan® EA-1340 Solution and Sterilization Procedures on Biomass Production The objectives of this study were to examine the effects of medium age, the age of Floxan® solutions and sterilization procedures on the ability of Floxan® EA-1340 to enhance biomass production.

All experiments were done in R70-3 medium with 2% (v/v) CSL, 10 g/L glucose, 25 mM DMG and 0.005% (v/v) Tween 80. Unless otherwise indicated, the concentration of Floxan® EA-1340 in each experiment was 1 g/L.

Strain 1306-21 was used for each experiment, and all pre-seed and seed cultures were grown in R70-3 plus 0.5% (w/v) TYE, 30 g/L glucose, 25 mM DMG and 0.1% (v/v) cellulase (Genencor).

In Experiment A, the effect of medium age on biomass was investigated. Biomass was compared from cultures grown in fresh medium (with and without protectant) and in 35-day old medium (with and without protectant). The results are summarized below:

TABLE 11

Effect of Medium Age on the Biomass Production of 1306-21 in R70-3 plus 2% CSL and 10 g/L Glucose (375 rpm) Day 3 Results

|  | Biomass (g/L) | Average Biomass (g/L) |
|---|---|---|
| Fresh Medium |  |  |
| 375 rpm Control | 3.21 | 3.33 |
| (No Protectant) | 3.46 |  |
| Floxan ® EA-1340 | 6.39 | 6.02 |
| (1 g/L) | 5.64 |  |
| 35 Days Old* |  |  |
| 375 rpm Control | 3.50 | 3.46 |
| (No Protectant) | 3.41 |  |
| Floxan ® EA-1340 | 5.28 | 5.28 |
| (1 g/L) |  |  |

*The same medium was used in both experiments.

Experiment A showed that the medium stored with Floxan ® EA-1340 in it deteriorated with time while no deterioration was observed in the medium without Floxan ® EA-1340.

Experiment B tested the effect of sterilizing the protectant in the presence of various medium components. The standard protocol used in previous experiments was to autoclave the Floxan ® EA-1340 in the presence of the four major salts (citrate, $KH_2PO_4$, $(NH_4)SO_4$ and $MgSO_4$), and to then add the CSL, trace salts, DMG, etc., as sterile additions. In this experiment, Floxan ® EA-1340 was autoclaved with different medium components and then tested for ability to enhance cellulose yield. In Experiment B, 0.4 g/L Floxan ® EA-1340 was used and all of the media was one day old.

The results are tabulated in Table 12.

TABLE 12

Effect of Protectant Sterilization on Biomass Production Strain 1306-21 in R70-3 plus 2% CSL, 10 g/L Glucose and 0.4 g/L Floxan ® EA-1340 Day 3 Results at 375 rpm

|  | Biomass (g/L) | Average Biomass (g/L) |
|---|---|---|
| 375 rpm Control | 3.38 | 3.38 |
| (No Protectant) |  |  |
| Control | 4.65 | 4.44 |
| (Major Salts) | 4.21 |  |
| Protectant-Water | 4.38 | 4.40 |
|  | 4.42 |  |
| Protectant-CSL | 4.06 | 3.75 |
|  | 3.45 |  |
| Protectant-Major | 4.06 | 4.12 |
| Salts + CSL | 4.19 |  |
| Protectant-Citrate | 4.36 | 4.37 |
|  | 4.37 |  |
| Protectant-$KH_2PO_4$ | 4.17 | 4.23 |
|  | 4.29 |  |
| Protectant-$MgSO_4$ | 4.45 | 4.35 |
|  | 4.25 |  |
| Protectant-$(NH_4)_2SO_4$ | 4.50 | 4.25 |
|  | 4.00 |  |

Experiment B shows that sterilizing the Floxan ® in the presence of CSL causes a significant reduction in the ability of the protectant to enhance cellulose production. Floxan ® sterilized in the presence of salts appears to retain the ability to enhance biomass production.

Experiment C tested the effect on biomass production of age of Floxan ® EA-1340 solutions. Floxan ® EA-1340 solutions were prepared, sterilized, and aged for varying lengths of time before being used in flask fermentations. Table 13 shows the results of this experiment.

TABLE 13

Effect of Age of Protectant Solutions on Biomass Production Strain 1306-21 in R70-3 plus 2% CSL 10 g/L Glucose and 1 g/L Floxan ® EA-1340 (375 rpm) Day 3 Results

|  | Biomass (g/L) | Average Biomass (g/L) |
|---|---|---|
| 375 rpm Control | 3.31 | 3.36 |
| (No Protectant) | 3.31 |  |
| Protectant Control | 5.62 | 5.47 |
| (Major Salts) | 5.32 |  |
| Protectant-Water | 5.86 | 5.70 |
| (Prepared and | 5.54 |  |
| autoclaved 2 |  |  |
| months prior to |  |  |
| use in fermentation) |  |  |
| Protectant-Water | 5.78 | 5.67 |
| (Prepared 2 | 5.57 |  |
| months prior to |  |  |
| autoclaving and |  |  |
| use in |  |  |
| fermentation) |  |  |
| Protectant-Water | 5.43 | 5.30 |
| (Prepared, | 5.18 |  |
| autoclaved and used |  |  |
| in fermentation |  |  |
| on same day) |  |  |

The ability of Floxan ® EA-1340 to enhance biomass production was not diminished upon storage of the Floxan ® in a water solution. The cultures to which the older protectant solutions were added had slightly higher biomass measurements than the cultures which received fresh protectant solutions. However, this may not be a significant variation.

The Chemap run in which the protectant Floxan ® EA-1340 was sterilized separately from CSL gave higher cellulose yield (0.29 g/g) in comparison to similar runs (two in which the protectant was sterilized with the CSL (see Table 9)).

Other modifications of the above described embodiments of the invention which are obvious to those of skill in the art of microbial fermentation and related disciplines are intended to be within the scope of the following claims.

What is claimed is:

1. A process for the aerobic production of microbial cellulose in an agitated culture of microbial cells capable of producing cellulose, grown in a suitable nutrient growth medium, wherein the process comprises the steps:
   - (a) culturing microbial cells in the presence of an agent comprising a polyacrylamide-containing polymer having a weight average molecular weight in the range of about $10^6$ to about $10^7$ daltons at a concentration effective to improve cellulose yield from an agitated culture; and
   - (b) recovering the microbially produced cellulose.

2. The process of claim 1 wherein the polyacrylamide-containing polymer is partially hydrolyzed to contain both carboxylate and carboxamide functional groups.

3. The process of claim 1 wherein the polyacrylamide-containing polymer is a co-polymer of sodium acrylate and acrylamide.

4. The process of claim 1 wherein the polyacrylamide-containing polymer is nonionic.

5. The process of claim 1 wherein the polyacrylamide containing polymer is anionic.

6. The process of claim 1 wherein the polyacrylamide containing polymer is low cationic.

7. The process of claim 1 wherein the microbial cells are bacteria.

8. The process of claim 7 wherein the bacteria are an Acetobacter species.

9. The process of claim 1 wherein the polyacrylamide-containing polymer is a sterile addition to sterile nutrient medium comprising a carbon source.

10. The process of claim 1 wherein the polyacrylamide containing polymer is mixed in an oil-in water emulsion.

11. The process of claim 1 wherein the polyacrylamide containing polymer is selected from the group consisting of Magnifloc ® 833A, Polytec 31, Polytec 36 and Floxan ® EA-1340.

12. The process of claim 1 wherein the polyacrylamide containing polymer is used in a concentration of about 0.1 to about 5 g/L, based on the initial culture medium volume.

13. The process of claim 1 wherein the microbial cells are recombinant cells.

14. The process of claim 1 wherein the cellulose is recovered by separating the cellulose from the cells using alkali treatment.

15. The process of claim 14 wherein the microbial culture is centrifuged and resuspended prior to the alkali treatment.

16. A process for the aerobic production of microbial cellulose in an agitated culture of microbial cells capable of producing cellulose, grown in a suitable nutrient growth medium, wherein the process comprises the steps:
(a) culturing microbial cells in the presence of an agent comprising a polyacrylamide-containing polymer having a molecular weight in the range of about $10^6$ to $10^7$ daltons at a concentration effective to improve cellulose yield from an agitated culture;
(b) agitating the microbial culture of (a) at rates at which cellulose yield is enhanced relative to analogous fermentations lacking the agent; and
(c) recovering the microbially produced cellulose.

17. A process for improving the mixing properties of an agitated culture of microbial cells wherein the process comprises culturing the microbial cells in the presence of an agent comprising a polyacrylamide-containing polymer having a molecular weight in the range of about $10^6$ to $10^7$ daltons at a concentration effective to improve the mixing properties of the agitated culture.

18. The process of claim 17 wherein the polyacrylamide containing polymer is Magnifloc ® 833A.

* * * * *